United States Patent
Davis et al.

(10) Patent No.: US 9,522,213 B2
(45) Date of Patent: Dec. 20, 2016

(54) PRESSURE-SENSITIVE HOT MELT ADHESIVE COMPOSITION INCLUDING PROPYLENE THERMOPLASTIC ELASTOMER AND ARTICLES INCLUDING THE SAME

(71) Applicant: H.B. Fuller Company, St. Paul, MN (US)

(72) Inventors: Kevin P. Davis, North St. Paul, MN (US); Ryan T. Gleason, Shoreview, MN (US); Peter Remmers, Hamburg (DE)

(73) Assignee: H.B. Fuller Company, St. Paul, MN (US)

( * ) Notice: Subject to any disclaimer, the term of this patent is extended or adjusted under 35 U.S.C. 154(b) by 207 days.

(21) Appl. No.: 13/920,347

(22) Filed: Jun. 18, 2013

(65) Prior Publication Data

US 2014/0371703 A1 Dec. 18, 2014

(51) Int. Cl.
| | |
|---|---|
| A61F 13/15 | (2006.01) |
| A61L 15/58 | (2006.01) |
| G09F 3/02 | (2006.01) |
| A61F 13/56 | (2006.01) |
| A61L 15/22 | (2006.01) |
| C09J 7/04 | (2006.01) |
| C09J 123/16 | (2006.01) |
| C09J 7/02 | (2006.01) |
| A61F 13/00 | (2006.01) |

(52) U.S. Cl.
CPC .......... *A61L 15/585* (2013.01); *A61F 13/5611* (2013.01); *A61L 15/225* (2013.01); *C09J 7/021* (2013.01); *C09J 7/045* (2013.01); *C09J 123/16* (2013.01); *G09F 3/02* (2013.01); *A61F 2013/00757* (2013.01); *A61L 2420/06* (2013.01); *C08L 2207/04* (2013.01); *C09J 2400/163* (2013.01); *C09J 2400/226* (2013.01); *C09J 2400/263* (2013.01); *C09J 2423/10* (2013.01); *G09F 2003/0241* (2013.01); *Y10T 428/1476* (2015.01); *Y10T 428/2804* (2015.01); *Y10T 428/2878* (2015.01); *Y10T 442/2754* (2015.04)

(58) Field of Classification Search
CPC ............ A61F 2013/00748; A61F 2013/00757
USPC ........................................ 604/366, 372, 373
See application file for complete search history.

(56) References Cited

U.S. PATENT DOCUMENTS

| | | | |
|---|---|---|---|
| 3,987,122 A | 10/1976 | Bartz et al. | |
| 5,418,052 A * | 5/1995 | Sugie | C09J 153/025 428/335 |
| 6,143,818 A | 11/2000 | Wang et al. | |
| 6,489,400 B2 | 12/2002 | Khandpur et al. | |
| 6,657,000 B1 | 12/2003 | De Keyzer et al. | |
| 6,747,114 B2 | 6/2004 | Karandinos et al. | |
| 6,833,404 B2 | 12/2004 | Quinn et al. | |
| 6,872,279 B1 | 3/2005 | Kolowrot et al. | |
| 7,199,180 B1 | 4/2007 | Simmons et al. | |
| 7,294,681 B2 | 11/2007 | Jiang et al. | |
| 7,521,507 B2 | 4/2009 | Lewtas et al. | |
| 7,700,707 B2 | 4/2010 | Abhari et al. | |
| 7,989,543 B2 | 8/2011 | Karjala et al. | |
| 2003/0096896 A1 | 5/2003 | Wang et al. | |
| 2007/0135563 A1 | 6/2007 | Simmons et al. | |
| 2007/0202330 A1* | 8/2007 | Peng | C08L 23/04 428/375 |
| 2008/0076860 A1* | 3/2008 | Ahmed et al. | 524/275 |

FOREIGN PATENT DOCUMENTS

| | | |
|---|---|---|
| EP | 0 178 062 | 4/1986 |
| EP | 1 700 895 | 9/2006 |
| WO | WO 00/01745 | 1/2000 |
| WO | WO 2011/022523 | 2/2011 |
| WO | WO2012/129489 | 9/2012 |

OTHER PUBLICATIONS

Eastman Chemical Company, "Eastotac H-142w Resin" (Apr. 2, 2012) (2 pages).
ExxonMobil Chemical, "Vistamaxx 6102 Propylene-based Elastomer" (Revised Jan. 22, 2013) (2 pages).
ExxonMobil Chemical, "Vistamaxx 6202 Propylene-based Elastomer" (Revised Jan. 22, 2013) (2 pages).
ExxonMobil Chemical, "Escorez 5400 Tackifying Resin" (Date Unknown) (1 page).
Eastman Chemical Company, "Eastotac H-130W Resin" (Apr. 2, 2012) (2 pages).
ExxonMobil Chemical, "Vistamaxx 3000 Propylene-based Elastomer" (Revised Jan. 22, 2013) (2 pages).
Kraton Polymers, "Kraton G1657 M Polymer" (Jul. 31, 2009) (2 pages).
ExxonMobil Chemical, "Escorez 2510 Tackifying Resin" (Dec. 2006) (1 page).
Eastman Chemical Company, "Piccotac 1115 Hydrocarbon Resin" (Aug. 14, 2006) (2 pages).
ExxonMobil Chemical, "Vistamaxx 3980FL Propylene-based Elastomer" (Revised Jan. 22, 2013) (2 pages).

* cited by examiner

*Primary Examiner* — Jacqueline Stephens

(74) *Attorney, Agent, or Firm* — Kirsten Stone; Allison Johnson

(57) ABSTRACT

A pressure-sensitive hot melt adhesive composition is disclosed that includes at least 10% by weight of a first propylene thermoplastic elastomer, at least 25% by weight of a first tackifying agent exhibiting a softening point of at least 120° C., and at least 25% by weight plasticizer.

38 Claims, No Drawings

PRESSURE-SENSITIVE HOT MELT ADHESIVE COMPOSITION INCLUDING PROPYLENE THERMOPLASTIC ELASTOMER AND ARTICLES INCLUDING THE SAME

BACKGROUND

The application is directed to preparing pressure-sensitive hot melt adhesive compositions that include propylene thermoplastic elastomers.

Positioning adhesives are used on disposable feminine hygiene articles to position the article on an undergarment. Typical positioning adhesives are based on styrene block copolymers such as a styrene-butadiene-styrene block copolymers and styrene-isoprene-styrene block copolymers.

Pressure-sensitive adhesives formulated with polyolefin polymers tend to exhibit weak cohesive properties and transfer in significant amounts to undergarments. Therefore polyolefin-based pressure-sensitive adhesives traditionally have not been used to as positioning adhesives.

There is a need for a pressure-sensitive adhesive that exhibits good tack, yet exhibits little to no adhesive transfer to undergarments.

SUMMARY

In one aspect, the invention features a pressure-sensitive hot melt adhesive composition that includes at least 10% by weight of a first propylene thermoplastic elastomer, at least 25% by weight plasticizer, and at least 25% by weight of a first tackifying agent exhibiting a softening point of at least 120° C. In one embodiment, the composition exhibits an initial peel force to cotton of at least 100 grams force per 25 millimeters. In seine embodiments, the composition exhibits a change in peel force to cotton after aging for two weeks at 50° C. relative to an initial peel force of no greater than 20%. In other embodiments, the composition exhibits an adhesive transfer of no greater than 50 gram force.

In some embodiments, the composition has an oil bleed rating of no greater than 3 when tested according to the Oil Bleed test method. In other embodiments, the composition is free from oil bleed when tested according to the Oil Bleed test method.

In some embodiments, the first tackifying agent exhibits a softening point of at least 130° C. In other embodiments, the first tackifying agent exhibits a softening point of at least 135° C.

In one embodiment, the composition disclosed herein further includes a second tackifying agent. In some embodiments, the second tackifying agent exhibits a softening point of no greater than 100° C.

In another embodiment, the composition further includes a polymer that exhibits a viscosity of no greater than 10,000 centipoise at 190° C. and a softening point greater than 90° C.

In other embodiments, the composition further includes a polymer that includes at least one of a thermoplastic polyolefin and a wax.

In one embodiment, the first propylene thermoplastic elastomer exhibits a melt index of no greater than 20 grams per 10 minutes. In another embodiment, the first propylene thermoplastic elastomer exhibits a melt index of no greater than 10 grams per 10 minutes. In other embodiments, the first propylene thermoplastic elastomer exhibits a density of no greater than 0.88 grams per cubic centimeter. In some embodiments, the first propylene thermoplastic elastomer includes a polypropylene-polyethylene copolymer.

In some embodiments, the composition further includes a second propylene thermoplastic elastomer different from the first propylene thermoplastic elastomer. In one embodiment, the second propylene thermoplastic elastomer includes a propylene-ethylene copolymer.

In other embodiments, the composition further includes a hydrogenated styrene block copolymer. In some embodiments, the composition further includes at least one of styrene-ethylene-butene-styrene block copolymer, styrene-ethylene-propylene-styrene block copolymer, and styrene-ethylene-ethylene-propylene-styrene block copolymer. In other embodiments, the composition further includes no greater than 10% by weight of at least one of styrene-ethylene-butene-styrene block copolymer, styrene-ethylene-propylene-styrene block copolymer, and styrene-ethylene-ethylene-propylene-styrene block copolymer.

In one embodiment, the composition includes from 25% by weight to no greater than about 55% by weight of the first tackifying agent, and from 10% by weight to no greater than about 20% by weight of the first propylene thermoplastic elastomer. In other embodiments, the composition further includes no greater than 20% by weight of a second tackifying agent exhibiting a softening point of no greater than 100° C. In other embodiments, the composition further includes no greater than 20% by weight of a polymer exhibiting a viscosity of no greater than 10,000 centipoise at 190° C. and a softening point greater than 90° C. In some embodiments, the composition exhibits a viscosity of no greater than 20,000 centipoise at 149° C.

In another aspect, the invention features an article that includes a substrate, and a pressure-sensitive adhesive composition disclosed herein disposed on the substrate. In one embodiment, the substrate includes a nonwoven web. In other embodiments, the article is a disposable absorbent article that includes the substrate and the pressure-sensitive adhesive composition disposed on the substrate, the disposable absorbent article being at least one of a diaper, a personal hygiene article, sanitary napkin, and a panty liner. In some embodiments, the substrate includes at least one of a polymer film, a metal film, and a metal foil.

In one embodiment, the article is in the form of a label, the substrate is a first substrate, and the pressure-sensitive adhesive composition is disposed between the first substrate and a release coated surface of a second substrate.

In another embodiment, the composition exhibits an initial peel force to stainless steel of at least 1 Newton.

In other aspects, the invention features an absorbent article that includes a topsheet, a backsheet, an absorbent core disposed between the topsheet and the backsheet, a garment-facing surface, and a pressure-sensitive adhesive composition disclosed herein disposed on the garment-facing surface of the absorbent article.

The invention features a pressure-sensitive hot melt adhesive composition that exhibits minimal transfer to cotton fabric.

Other features and advantages will be apparent from the following description of the preferred embodiments and from the claims.

DETAILED DESCRIPTION

The pressure-sensitive hot melt adhesive composition includes a propylene thermoplastic elastomer, plasticizer, and a tackifying agent that exhibits a softening point of at least 120° C.

The composition preferably exhibits an initial peel force to cotton of at least about 70 grams force per 25 millimeters (gf/25 mm), at least about 100 gf/25 mm, at least about 125 gf/25 mm, at least about 150 gf/25 mm, or even at least about 200 gf/25 mm, and a change in peel force after aging for two weeks at 50° C. of no greater than 30%, of no greater than 20%, no greater than 15% or even no greater than 10% relative to its initial peel force to cotton.

The adhesive composition preferably is suitable for use as a positioning adhesive, which is a class of adhesive compositions that is often used to position feminine hygiene articles, such as sanitary napkins, on undergarments, e.g., cotton undergarments. These articles are removed from the undergarment after use. When the article is removed from the undergarment, preferably no adhesive composition remains on the undergarment (i.e., the undergarment is free of adhesive transfer). However, in some instances, the adhesive fails cohesively and small spots of adhesive composition might remain on the undergarment. These spots usually are randomly located and vary in dimension. The Adhesive Transfer Test Method provides one useful measure of the amount of adhesive composition that has transferred to the undergarment. The adhesive composition preferably exhibits an adhesive transfer of no greater than 50 gf, no greater than 40 gf, no greater than 30 gf, no greater than 20 gf, or even no greater than 10 gf when tested according the Adhesive Transfer Test Method.

The composition optionally exhibits an initial peel force to stainless steel of at least about 1 Newton (N).

The composition also preferably exhibits a viscosity of no greater than about 20,000 centipoise (cP), no greater than about 15,000 cP, or even no greater than about 10,000 cP at 149° C.

The composition also preferably has an oil bleed rating of no greater than 3, no greater than 2 or even is free of oil bleed when tested according to the Oil Bleed test method.

The composition optionally exhibits a shear adhesion failure temperature (SAFT) of at least 40° C., at least 45° C. or even at least 50° C.

Propylene Thermoplastic Elastomer

The propylene thermoplastic elastomer exhibits a melt flow rate of no greater than 30 g/10 min or even no greater than 20 g/10 min at 230° C. when measured according to ASTM D1238, and a density of at least 0.86 g/cm$^3$, at least 0.87 g/cm$^3$, no greater than 0.88 g/cm$^3$, or even from about 0.86 g/cm$^3$ to about 0.88 g/cm$^3$.

Suitable propylene thermoplastic elastomers include polypropylene homopolymers and higher order polymers (e.g., copolymers and terpolymers) derived from propylene and at least one olefin co-monomer. Examples of suitable olefin co-monomers include C2-C12 α-olefin monomers including, e.g., ethylene, butylene, isobutylene, 1-butene, pentene, 1-hexene, 4-methyl-1-pentene, 1-heptene, 1-octene, nonene, decene, dodecene, cyclopentene, cyclohexene, cyclooctene, 3-methyl pentene-1,3,5,5-trimethylhexene-1,5-ethyl-1-nonene, and combinations thereof. The propylene thermoplastic elastomer preferably includes at least 50% by weight propylene.

Useful examples of propylene thermoplastic elastomers include polypropylene, propylene/ethylene copolymers, propylene/ethylene/butene terpolymers, propylene/butene copolymers, propylene/hexene, propylene/octene, propylene/norbornene, and combinations thereof.

Useful propylene thermoplastic elastomers include, e.g., single-site (e.g., metallocene) catalyzed propylene thermoplastic elastomers.

Suitable propylene thermoplastic elastomers are commercially available under a variety of trade designations including, e.g., VISTAMAXX from ExxonMobil Chemical Company (Houston, Tex.) including, e.g., VISTAMAXX 6102 polypropylene, VISTAMAXX 6202 propylene-ethylene copolymer, VISTAMAXX 3000 propylene-ethylene copolymer, and VISTAMAXX 3980, and the NOTIO trade designations from Mitsui (Japan) including NOTIO PN-2070.

The composition includes at least 10% by weight, no greater than about 20% by weight, from about 11% by weight to about 18% by weight, or even from about 10% by weight to no greater than about 20% by weight propylene thermoplastic elastomer.

Plasticizer

Suitable plasticizers for use in the composition include, e.g., mineral oil, paraffin oil, synthetic liquid oligomers of polyolefins (e.g., polybutene and polypropylene), hydrocarbon fluids, vegetable oil, and combinations thereof.

Useful commercially available plasticizers include, e.g., plasticizers sold under the NYFLEX series of trade designations from Nynas Corporation (Houston, Tex.) including, e.g., NYFLEX 222B, KAYDOL OIL from Sonneborn, LLC (Parsippany, N.J.), KRYSTOL 550 mineral oil from Petrochem Carless Limited (Surrey, England), CALSOL 550 oil from Calumet Specialty Products Partners, LP (Indianapolis, Ind.), and under the SPECTRASYN series of trade designations from ExxonMobil Chemical Company (Houston, Tex.) including, e.g., SPECTRASYN 4 and 40.

The composition includes at least 25% by weight, at least about 30% by weight, at least about 35% by weight, or even at least about 40% by weight plasticizer.

Tackifying Agent

The tackifying agent has a softening point of at least 120° C., at least 125° C., at least 130° C., or even at least 140° C. Suitable classes of tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; and combinations thereof. Examples of useful aliphatic and cycloaliphatic petroleum hydrocarbon resins include aliphatic and cycloaliphatic petroleum hydrocarbon resins include, e.g., branched and unbranched C9 resins and C10 resins and the hydrogenated derivatives thereof. Examples of useful polyterpene resins include hydrogenated polyterpene resins, and copolymers and terpolymers of natural terpenes (e.g. styrene-terpene, alphamethyl styrene-terpene and vinyl toluene-terpene).

Useful tackifying agents are commercially available under a variety of trade designations including, e.g., ESCOREZ from Exxon Mobil Chemical Company (Houston, Tex.) including, e.g., ESCOREZ 5637 and 5340, and EASTOTAC from Eastman Chemical (Kingsport, Tenn.) including, e.g., EASTOTAC H-130W and H-142W.

The composition includes at least 25% by weight, at least about 30% by weight, at least about 35% by weight, no greater than about 55% by weight, from about 30% by weight to at least about 50% by weight, or even from about 35% by weight to about at least about 45% by weight tackifying agent having a softening point of at least 120° C.

The composition optionally includes a second tackifying agent. The second tackifying agent preferably has a softening point no greater than 100° C. Suitable classes of tackifying agents having a softening point no greater than 100° C. include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof; low molecular weight polylactic acid; and combinations thereof. Examples of useful aliphatic and cycloaliphatic petroleum hydrocarbon resins include aliphatic and cycloaliphatic petroleum hydrocarbon resins (e.g., branched and unbranched C5 resins, C9 resins, and C10 resins) and the hydrogenated derivatives thereof. Examples of useful natural and modified rosins include gum rosin, wood rosin, tall oil rosin, distilled rosin, hydrogenated rosin, dimerized rosin, and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin. Examples of useful polyterpene resins hydrogenated polyterpene resins, and copolymers and terpolymers of natural terpenes (e.g. styrene-terpene, alpha-methyl styrene-terpene and vinyl toluene-terpene).

Useful tackifying agents having a softening point no greater than 100° C. are commercially available under a variety of trade designations including, e.g., the ESCOREZ series of trade designations from ExxonMobil Chemical Company (Houston, Tex.) including, e.g., ESCOREZ 5690, 5400, 2510, and 2203, the EASTOTAC series of trade designations from Eastman Chemical (Kingsport, Tenn.) including, e.g., EASTOTAC H-100R and H-100L, the WINGTACK series of trade designations from Cray Valley HSC (Exton, Pa.) including, e.g., WINGTACK 86, EXTRA and 95, and the PICCOTAC series of trade designations from Eastman Chemical Company (Kingsport, Tenn.) including, e.g., PICCOTAC 8095.

When present, the composition includes no greater than about 20% by weight, no greater than about 15% by weight, or even from about 5% by weight to no greater than about 15% by weight tackifying agent having a softening point of no greater than 100° C.

High Softening Point Component

The composition optionally includes a component that has a softening point greater than 90° C. and a viscosity of no greater than 10,000 centipoise at 190° C., useful examples of such components include certain waxes and polymers. For ease of reference this component is also referred to herein as a high softening point component (e.g., high softening point polymer and high softening point wax). The high softening point component preferably increases the cohesive strength of the composition relative to the composition without the high softening point polymer. Useful high softening point polymers include, e.g., thermoplastic polymers (e.g., polyolefins (e.g., polyethylene, polyethylene copolymers, polypropylene, propylene-ethylene copolymers, propylene-butene copolymers, polypropylene-hexene copolymers, polypropylene-octene, copolymers and combinations thereof), polyvinyl acetate, and combinations thereof. Useful high softening point polymers are commercially available under a variety of trade designations including, e.g., the L-MODU trade designation from Idemitsu Kosan Co., Ltd (Japan) including, e.g., L-MODU 5400 polypropylene, and the LICOCENE series of trade designations from Clariant Int'l Ltd. (Muttenz, Switzerland) including, e.g., LICOCENE PP 1602 TP and PP 2602 TP polypropylene.

Useful high softening point waxes include, e.g., polyolefin waxes (e.g., polypropylene waxes, polyethylene waxes, high density low molecular weight polyethylene waxes, and by-product polyethylene waxes)), microcrystalline waxes, paraffin waxes, metallocene waxes, vegetable waxes, animal waxes, stearamide waxes, glycerin monostearate, sorbitan monostearate, and combinations thereof. Useful high softening point waxes are commercially available under a variety of trade designations including, e.g., waxes that are commercially available under the EPOLENE series of trade designations from Westlake Chemical Corporation (Houston, Tex.) including, e.g., EPOLENE N-21 and N-14 polyethylene waxes, and the AC series of trade designations from Honeywell Int'l Inc. (Morristown, N.J.) including, e.g., A-C 8 and A-C 9 polyethylene waxes.

When present, the composition preferably includes no greater than about 20% by weight, no greater than about 10% by weight, no greater than about 8% by weight, or even from about 1% by weight to no greater than about 10% by weight high softening point polymer, high softening point wax, or a combination thereof.

Hydrogenated Styrene Block Copolymers

The composition optionally includes hydrogenated styrene block copolymer. Useful hydrogenated styrene block copolymers include, e.g., styrene-ethylene/butene-styrene block copolymer, styrene-ethylene/propylene-styrene block copolymer, styrene-ethylene/ethylene/propylene-styrene block copolymer, styrene-ethylene/butene diblock copolymers, styrene-ethylene/propylene diblock copolymers, and combinations thereof. Suitable hydrogenated styrene block copolymers are commercially available under a variety of trade designations including, e.g., the SEPTON series of trade designations from Kuraray Co. Ltd (Japan) including, e.g., SEPTON 52063 and 52007 styrene-ethylene/propylene-styrene block copolymers, and the KRATON G series of trade designations from Kraton Performance Polymers Inc. (Houston, Tex.) including, e.g., KRATON G 1657 styrene-ethylene/butene-styrene block copolymers.

When present, the composition preferably includes no greater than about 10% by weight, no greater than about 8% by weight, or even from about 1% by weight to no greater than about 8% by weight hydrogenated styrene block copolymer.

Other Optional Components

The composition can optionally include a variety of additional components including, e.g., stabilizers, antioxidants, adhesion promoters, ultraviolet light stabilizers, rheology modifiers, biocides, corrosion inhibitors, dehydrators, colorants (e.g., pigments and dyes), fillers, surfactants, flame retardants, additional waxes, additional polymers (e.g., styrene-isoprene-styrene and styrene-butadiene-styrene block copolymers), and combinations thereof.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J.), and ETHYL 702 4,4'-methylene bis(2,6-di-tert-butylphenol), and the BNX series of trade designations including, e.g., BNX 1010 and BNX 1076 from Mayzo, Inc. (Suwanee, Ga.). When present, the adhesive composition preferably includes from about 0.1% by weight to about 2% by weight antioxidant.

Use

The pressure-sensitive adhesive composition is useful as a positioning adhesive disposed on at least one substrate surface of a disposable absorbent article and can be used to position an absorbent article on a garment such as underwear. Such disposable absorbent articles include, e.g., feminine hygiene articles such as sanitary napkins and panty liners, diapers, disposable garments having a waist opening and leg openings, and adult incontinence articles. In one construction, the absorbent article (e.g., a feminine hygiene article) includes a garment facing surface and a body facing surface, a topsheet having a garment facing surface and a body facing surface, a backsheet having a garment facing surface and a body facing surface, and an absorbent core disposed between the body facing surface of the backsheet and the garment facing surface of the topsheet. The pressure-sensitive adhesive composition is disposed on the garment facing surface of the adsorbent article, in general, or even on the garment facing surface of the backsheet, in particular. A release liner optionally is disposed on the pressure-sensitive hot melt adhesive composition to protect the pressure-sensitive adhesive composition until use. The absorbent article (e.g., a feminine hygiene article) optionally includes additional layers and adhesives and the components of the absorbent article optionally exhibit additional functionality. Examples of additional layers, functionality and combinations thereof include dusting, wicking, acquisition, additional top sheets, multiple core layers, superabsorbent particles and compositions, wetness indicators, and combinations thereof.

The composition is also useful in a variety of other applications and constructions including, e.g., forming permanent bonds, temporary bonds (e.g., removable and repositionable adhesive applications), medical dressings (e.g., wound care products), bandages, surgical pads, drapes, gowns, labels (e.g., pressure-sensitive adhesive labels), tapes (e.g., pressure-sensitive adhesive tapes), filters (e.g., pleated filters and filter frames), and combinations thereof.

The composition is useful in a variety of forms including, e.g., as a coating (e.g., continuous and discontinuous (e.g., random, pattern, array, spiral, dots, spots, and combinations thereof) coatings), film (e.g., continuous films and discontinuous films), bead, sheet, fiber, filament, web (e.g., woven and nonwoven), and combinations thereof.

The composition also can be applied to a variety of substrates including, e.g., films (e.g., polyolefin (e.g., polyethylene and polypropylene), polyester, metallized polymer, multilayer, biaxially oriented, monoaxially oriented, ethylene-vinyl acetate copolymer, polyurethane, vinyl, polyvinylidene fluoride, cellulose acetate and ethyl cellulose, and polyamide films, and combinations thereof), metal foils, release liners, porous substrates, cellulose substrates, sheets (e.g., paper and fiber sheets), paper products, woven and nonwoven webs, fibers (e.g., natural cellulose fibers such as wood pulp, cotton, silk and wool; cellulosic fibers; synthetic polymer fibers such as nylon, rayon, polyesters, acrylics, polypropylenes, polyethylene, polyvinyl chloride, and polyurethane; glass fibers; recycled fibers; and various combinations thereof), and tape backings. Useful substrates include, e.g., single layer, multilayer, treated (e.g., corona treated or chemically primed), and untreated substrates, and combinations thereof.

Various application techniques can be used to apply the adhesive composition to a substrate including, e.g., slot coating, spraying (e.g., spiral spraying and random spraying), screen printing, foaming, engraved roller, extrusion, meltblown adhesive application techniques, and combinations thereof.

The invention will now be described by way of the following examples. All parts, ratios, percentages and amounts stated in the Examples are by weight unless otherwise specified.

EXAMPLES

Test Procedures

Test procedures used in the examples include the following. All ratios and percentages are by weight unless otherwise indicated. The procedures are conducted at room temperature (i.e., an ambient temperature of from about 20° C. to about 25° C.) unless otherwise specified. The properties set forth for the components used in the compositions are as reported by the manufacturer unless otherwise specified.

Test Procedures

Viscosity Test Method

Viscosity is determined in accordance with ASTM D-3236 entitled, "Standard Test Method for Apparent viscosity of Hot Melt Adhesives and Coating Materials," (Oct. 31, 1988), using a Brookfield Thermosel viscometer Model RVDV 2, and a number 27 spindle. The results are reported in centipoise (cP).

Test Sample Preparation Method for Peel Force to Cotton and Adhesive Transfer Test Methods A laminate is prepared by coating a sample composition onto a Mylar release film in a one inch wide pattern at an add-on weight of 20 grams per square meter (g/m$^2$) (+/−3 g/m$^2$) using a slot applicator and then contacting the adhesive strip with the treated side of a 1 mil (0.025 mm) thick polyethylene film to form a Mylar film/adhesive/polyethylene film laminate. Test samples having a length of 4 inches (in) (10.16 cm) in the machine direction and 1.5 in (3.81 cm) in the cross-machine direction are then cut from the laminate such that the adhesive pattern is centered in the cross-machine direction of the test sample.

Strips of cotton fabric having a length of 4 in (10.16 cm) in the machine direction and a width of 1.5 in (3.81 cm) in the cross-machine are cut from 124 g/m$^2$ bleached t-shirt cotton fabric (Testfabrics, Inc., West Pittston, Pa.). Before cutting the cotton fabric, the grid work of the stitching of the fabric is examined. When the cotton fabric is stretched, the sample will exhibit greater elongation in one direction than in another direction. The cotton fabric is cut lengthwise in the direction that has less elongation. All cotton fabric strips are cut as straight as possible along the stitching grid work. If the cotton fabric strips are cut askew, an inconsistent elongation of the cotton fabric test sample will result.

The release film is removed from the adhesive and the adhesive side of each test sample is gently placed on the surface of a cotton strip such that the cotton curls up (in the lengthwise direction) toward the adhesive bond to form the composite test sample. In preparing the composite test sample, the adhesive is not pressed down onto the cotton fabric.

Peel Force to Cotton Test Method

Seven samples are prepared according to the Peel Force and Adhesive Transfer Test Sample Preparation Method. The test sample is placed on a 2 kg mechanical roll-down device and the roller is allowed to pass over the film side of the sample two times, once in the forward direction and once in the backward direction, at a rate of 305 mm/min. A timer is then activated and the sample is placed into the jaws of INSTRON-type peel tester. The polyethylene film is placed into the moving jaw, and the cotton fabric is attached to the stationary jaw. Within one minute after the sample has been removed from the roll-down device, the sample is tested according to ASTM D1876-01 entitled, "Test Method for Determining Peel Resistance of Adhesive (T-Peel Test Method)," with the exception that the test is run at a rate of 305 mm/min, instead of 250 mm/min, over a period of ten seconds, and seven replicates are run instead of the ten specified in ASTM D1876. The average peel force over ten seconds of peeling is recorded, and the results are reported in grams.

The initial peel force is measured 24 hours after the test sample is prepared. The two week peel force is measured after the test sample has been subjected to accelerated aging at 50° C. for two weeks. The four week peel force is measured after the test sample has been subjected to accelerated aging at 50° C. for four weeks.

Adhesive Transfer Test Method

Seven test samples are prepared according to the Peel Force and Adhesive Transfer Test Sample Preparation. Brass weights (5 kg each), two glass plates (10 cm×12 cm×0.4 cm each), and a foamed rubber mat (10 cm×12 cm×0.3 cm each) are preconditioned in an oven at 38° C. for at least one hour before starting the test. The foamed rubber is placed on top of the first glass plate, and the seven test samples are then stacked one on top of another, ensuring that the adhesive patterns are aligned and the thickness across the glass plate is equal. For each sample, the area of adhesive to which pressure is applied is 2.5 cm by 6 cm. Since the glass plates are 12 cm long, two stacks of seven test samples are aligned across the length of the glass plate. The second glass plate is placed on top of the stacked samples and the 5 kg brass weight is set on top of the glass to allow even distribution of pressure across the area of the adhesive. The pressure applied to the adhesive is approximately 1666 kg/m$^2$. The samples are then put in an oven at 38° C. for five hours. After this period of time, the weight is removed from the glass plates and the samples are taken from the oven and conditioned at 23° C. and 50% relative humidity for at least one hour. The samples are then tested using an INSTRON-type tensile testing apparatus at 500 mm/min for 100 mm. The full length of the test sample is peeled using the INSTRON apparatus.

The amount of adhesive residue that remains on the cotton fabric test strip (i.e., the transferred adhesive) is then quantified as follows. The side of the cotton fabric test strip that had been in contact with the adhesive is contacted with the treated side of a 0.5 mil (0.0125 mm) thick polyethylene film to form a composite. This composite is placed on a 2 kg mechanical roll-down device, and the roller is allowed to pass over the film side of the sample two times, once in the forward direction and once in the backward direction, at a rate of 305 mm/min. A timer is then activated and the sample is placed into the jaws of INSTRON-type peel tester. The polyethylene film is placed into the moving jaw, and the cotton fabric is attached to the stationary jaw. Within one minute after the sample has been removed from the roll-down device the sample is peeled at a rate of 305 min/min for a length of 100 mm. The peak peel force is recorded, and the results are reported as the adhesive transfer in gram force (gf).

Peel Force to Stainless Steel Sample Preparation Method

A laminate is prepared by coating a sample composition onto an untreated Mylar film in a one inch wide pattern at an add-on weight of 20 g/m$^2$ using a slot applicator and then contacting the adhesive strip with the treated side of a 2 mil (0.05 mm) thick Mylar release film to form a release treated Mylar/adhesive/untreated Mylar film laminate. Test samples having a length of 84 inches (in) (23.32 cm) in the machine direction and 10.5 in (3.81 cm) in the cross-machine direction are then cut from the laminate such that the adhesive pattern is centered in the cross-machine direction of the test sample.

The release layer is then removed and the adhesive is applied to a stainless steel panel having a length of 8 in (20.32 cm) and a width of 3 in (7.62 cm). In preparing the composite test sample, the adhesive is not pressed down onto the stainless steel.

Peel Force to Stainless Steel Test Method

Three samples are prepared according to the Peel Force to Stainless Steel Sample Preparation Method. Each test sample is placed on a 2 kg mechanical roll-down device and the roller is allowed to pass over the film side of the sample two times, once in the forward direction and once in the backward direction, at a rate of 305 mm/min. A timer is then activated and the sample is placed into the jaws of INSTRON-type peel tester. After one minute, the sample is peeled at a 180 degree angle according to PSTC 101 entitled, "Peel Adhesion of Pressure Sensitive Tape," and the peel force is recorded. The average peel force of the three samples is reported in Newtons (N).

Shear Adhesion Failure (SAFT) Test Sample Preparation

Adhesive laminates used for SAFT testing are prepared by coating a sample composition on a Mylar release film in a one inch wide pattern and at an add-on weight of 20 g/m$^2$ using a slot applicator. The adhesive is then transferred to an untreated Mylar film (i.e., a Mylar film without release properties) to form a Mylar film/adhesive/Mylar film laminate. Samples are then cut from the laminate to a length of one inch in the machine direction and three inches in the cross-machine direction such that the adhesive is present at one end of the sample.

The Mylar release film is then removed from each of two samples to expose the one square inch area of the adhesive present on the end of each sample. The exposed adhesive of a first sample is then contacted with the exposed adhesive of a second sample to form a test sample that is five inches long and has a one inch overlap in the center. The adhesive overlap has an area of 2.54 cm$^2$ and a total add-on level of 40 g/m$^2$.

SAFT Test Method

Test samples are prepared according to the SAFT Test Sample Preparation Method. Each test sample is placed on a 2 kg mechanical roll-down device, and the roller is allowed to pass twice over the sample, once in the forward direction and once in the backward direction, at a rate of 305 mm/min.

The shear adhesion failure (SAFT) of the test sample is determined by placing a test sample in a programmed oven, applying a shear force with a 500 g weight and ramping the temperature up from 25° C. to 175° C. at a rate of 25° C. per hour according to ASTM D-4498 entitled, "A Standard Test Method for the Heat-fail Temperature in Shear of Hot Melt Adhesives." The oven automatically records the temperature at which the test sample fails. The result reported is the average failure temperature of four test samples. The result is reported in degrees Celsius.

Oil Bleed Test Method

The adhesive composition is placed in the oven at 163° C. until it is molten and free of air bubbles. The test sample is prepared by pouring 5 g±0.1 g onto the release surface of a piece of wax paper. The sample is allowed to cool to room temperature. A sheet of HP Multipurpose 75 g/m² printing paper (Hewlett Packard Development Company, LP, Palo Alto, Calif.) (or equivalent) is placed on top of the adhesive surface of the sample, the sample is then set on a metal tray, and then a 1 kg weight is placed on top of the sample such that the wax paper is between the weight and the adhesive of the sample. The sample is then conditioned in an oven at 49° C. for 70 hours, removed from the oven, and then conditioned at room temperature for one hour.

The sample is then visually observed to determine the amount of oil that has soaked in to the paper and the nature of the edges of the oil stain, if any. A rating is assigned based upon the observation. Table 1 below sets forth the criteria for each oil bleed rating.

TABLE 1

| Rating | Scale | Stain | Edges |
|---|---|---|---|
| 1 | Good | No evidence of oil present on the paper | Edges cannot be seen |
| 2 | Slight | Slight ghosting and darkening | Edges are noticeable but not well defined |
| 3 | Marginal | Significant darkening | Edges are very clear and distinct |
| 4 | Bad | Noticeable stain-dark, but the stain does not come through the paper | Edges are very clear and distinct |
| 5 | Very bad | Stain through paper | Edges are starting to bleed |

Examples 1-19

The adhesive compositions of Examples 1-19 were prepared by combining and mixing the components in the amounts set forth in Tables 2 and 3 in a sigma blade mixer operating at 177° C.

The adhesive compositions of Examples 1-19 were then tested according to at least one of the Viscosity, Peel Force to Cotton (initial and after aging for two weeks at 50° C. and 50% humidity), Peel Force to Stainless Steel, Adhesive Transfer, and SAFT test methods set forth above. The viscosity test method was conducted at 149° C., 163° C., and 177° C. The results are reported in Tables 4 and 5 below.

TABLE 2

| | Example | | | | | | |
|---|---|---|---|---|---|---|---|
| | 1 | 2 | 3 | 4 | 5 | 6 | 7 |
| VISTAMAXX 6202[1] | 15 | 12 | 15 | 15 | 15 | 15 | 15 |
| VISTAMAXX 6102[2] | 5 | 3 | 0 | 0 | 0 | 0 | 0 |
| SEPTON 2063[3] | 0 | 0 | 0 | 5 | 0 | 0 | 0 |
| L-MODU S400[4] | 0 | 0 | 5 | 0 | 5 | 5 | 5 |
| EASTOTAC H-142W[5] | 40 | 50 | 45 | 45 | 35 | 0 | 32 |
| ESCOREZ 5637[6] | 0 | 0 | 0 | 0 | 0 | 35 | 0 |
| ESCOREZ 2203LC[7] | 0 | 0 | 0 | 0 | 10 | 10 | 13 |
| EPOLENE N21[8] | 0 | 0 | 0 | 0 | 0 | 0 | 3 |
| CALSOL 550[9] | 39.8 | 34.8 | 34.8 | 34.8 | 34.8 | 34.8 | 31.8 |
| BNX 1076[10] | 0.2 | 0.2 | 0.2 | 0.2 | 0.2 | 0.2 | 0.2 |

[1] = propylene-based thermoplastic elastomer (ExxonMobil Chemical Company, Houston, Texas)
[2] = propylene-based thermoplastic elastomer (ExxonMobil)
[3] = hydrogenated styrenic block copolymer (Kuraray Co. Ltd, Japan)
[4] = propylene homopolymer (Idemitsu Kosan Company Ltd., Japan)
[5] = hydrogenated hydrocarbon resin having a ring and ball softening point of 142° C. as measured according to ASTM E 28 (Eastman Chemical Co.., Kingsport, Tennessee)
[6] = tackifying agent (ExxonMobil)
[7] = aromatic modified aliphatic hydrocarbon resin having a softening point of 92.6° C. measured according to ExxonMobil test method ETM 22-24, which is based on ASTM D-6090-97, as reported by ExxonMobil in the corresponding product literature (ExxonMobil)
[8] = polyethylene wax (Westlake Chemical Co, Houston, Texas)
[9] = naphthenic oil (Calumet Specialty Products Partners, LP, Indianapolis, Indiana)
[10] = antioxidant (Mayzo, Inc., Suwanee, Georgia)

TABLE 3

| | Example | | | | | | | | | | | |
|---|---|---|---|---|---|---|---|---|---|---|---|---|
| | 8 | 9 | 10 | 11 | 12 | 13 | 14 | 15 | 16 | 17 | 18 | 19 |
| VISTAMAXX 6202 | 20 | 11 | 10 | 20 | 16 | 15 | 20 | 15.3 | 20 | 16 | 10 | 10 |
| L-MODU S400 | 6 | 10 | 10 | 10 | 10 | 5 | 5 | 7.6 | 7.5 | 5 | 5 | 7.5 |
| EASTOTAC H-142W | 27 | 42 | 33 | 30 | 27 | 33 | 33 | 34.9 | 35.5 | 42 | 38 | 42 |
| ESCOREZ 2510[11] | 10 | 10 | 10 | 10 | 10 | 10 | 10 | 10 | 10 | 10 | 10 | 10 |
| CALSOL 550 | 36.8 | 26.8 | 36.8 | 29.8 | 36.8 | 36.8 | 36.8 | 32.1 | 26.8 | 26.8 | 36.8 | 30.3 |
| EVERNOX 76[12] | 0.2 | 0.2 | 0.2 | 0.2 | 0.2 | 0.2 | 0.2 | 0.2 | 0.2 | 0.2 | 0.2 | 0.2 |

[11] = aromatic modified aliphatic resin having a softening point range of from 92° C. to 97° C. measured according to ExxonMobil test method ETM 22-24, as reported by ExxonMobil in the corresponding product literature (ExxonMobil)
[12] = antioxidant (Everspring Chemical Co., Ltd., Taiwan)

TABLE 4

| | Example | | | | | | |
|---|---|---|---|---|---|---|---|
| | 1 | 2 | 3 | 4 | 5 | 6 | 7 |
| Viscosity (cP) | | | | | | | |
| 149° C. | 16,200 | 6,925 | 5,525 | 8,700 | 4,675 | 4,987 | 6,438 |
| 163° C. | 10,620 | 4,312 | 3,500 | 5,425 | 2,935 | 2,895 | 4,000 |
| 177° C. | 6,525 | 2,795 | 2,285 | 3,500 | 1,955 | 1,955 | 2,625 |
| Peel to Cotton (g) | | | | | | | |
| Initial | N.M. | 216 | 246 | 207 | 221 | 287 | N.M. |
| Aged | N.M. | 193 | 197 | 205 | 252 | 250 | N.M. |
| Peel to Stainless Steel (N) | 13.93 | 27.84 | 22.98 | 22.20 | 24.91 | 24.74 | 22.72 |
| Adhesive Transfer (gf) | 10 | 20 | 7 | 6 | 3 | 0 | 4 |
| SAFT (° C.) | 33.8 | 34.1 | 36.3 | 37.2 | 33.6 | 33.9 | 43.7 |
| Oil Bleed | 3 | 4 | 3 | 3 | 4 | 3 | 2 |

N.M. = Not Measured

TABLE 5

| | Example | | | | | | | | | | | |
|---|---|---|---|---|---|---|---|---|---|---|---|---|
| | 8 | 9 | 10 | 11 | 12 | 13 | 14 | 15 | 16 | 17 | 18 | 19 |
| Viscosity (cP) | | | | | | | | | | | | |
| 149° C. | 9750 | 3825 | 2090 | 13850 | 6425 | 4070 | 12100 | 6487 | 15400 | 14800 | 1795 | 2540 |
| 163° C. | 6241 | 2208 | 1300 | 9387 | 5400 | 2620 | 7150 | 4175 | 9675 | 9950 | 1060 | 1570 |
| 177° C. | 4366 | 1433 | 890 | 5825 | 3430 | 1790 | 4625 | 2725 | 6425 | 6550 | 735 | 1035 |
| Peel to cotton (g) | | | | | | | | | | | | |
| Initial | 101 | 106 | 121 | 85 | 73 | 143 | 117 | 164 | 136 | 144 | 185 | 147 |
| Aged | 67 | 90 | 109 | 80 | 73 | 128 | 104 | 143 | 115 | 121 | 141 | 124 |
| Adhesive Transfer (gf) | 0 | 14 | 0 | 0 | 0 | 0 | 0 | 0 | 0 | 4 | 2 | 3 |
| SAFT (° C.) | 46.4 | 46.4 | 37.6 | 55.4 | 43.9 | N.M. | 45.8 | 36.0 | 53.9 | 47.1 | 30.8 | 41.1 |
| Oil Bleed | 2 | 3 | 4 | 1 | 2 | 4 | 2 | 2 | 1 | 3 | 5 | 4 |

Documents referred to herein are incorporated herein to the extent they do not conflict.

Other embodiments are within the claims.

What is claimed is:

1. A pressure-sensitive hot melt adhesive composition comprising:
    at least 10% by weight of a first propylene thermoplastic elastomer comprising at least 50% by weight propylene;
    at least 25% by weight plasticizer; and
    at least 25% by weight of a first tackifying agent exhibiting a softening point of at least 120° C.

2. The pressure-sensitive adhesive composition of claim 1, wherein the composition exhibits an initial peel force to cotton of at least 100 gram force per 25 millimeters.

3. The pressure-sensitive adhesive composition of claim 1, wherein the composition exhibits a change in peel force to cotton, after aging for two weeks at 50° C. relative to an initial peel force, of no greater than 20%.

4. The pressure-sensitive adhesive composition of claim 1, wherein the composition exhibits an adhesive transfer of no greater than 50 gram force.

5. The pressure-sensitive adhesive composition of claim 1, wherein the composition has an oil bleed rating of no greater than 3 when tested according to the Oil Bleed test method.

6. The pressure-sensitive adhesive composition of claim 1, wherein the composition is free from oil bleed when tested according to the Oil Bleed test method.

7. The pressure-sensitive adhesive composition of claim 1, wherein the first tackifying agent exhibits a softening point of at least 130° C.

8. The pressure-sensitive adhesive composition of claim 1, wherein the first tackifying agent exhibits a softening point of at least 135° C.

9. The pressure-sensitive adhesive composition of claim 1 further comprising a second tackifying agent.

10. The pressure-sensitive adhesive composition of claim 9, wherein the second tackifying agent exhibits a softening point of no greater than 100° C.

11. The pressure-sensitive adhesive composition of claim 9, wherein the first tackifying agent comprises a hydrogenated hydrocarbon resin and the second tackifying agent comprises an aromatic modified aliphatic hydrocarbon resin.

12. The pressure-sensitive adhesive composition of claim 1 further comprising a polymer exhibiting a viscosity of no greater than 10,000 centipoise at 190° C. and a softening point greater than 90° C.

13. The pressure-sensitive adhesive composition of claim 1 further comprising a polymer comprising a thermoplastic polyolefin, a wax, or a combination thereof.

14. The pressure-sensitive adhesive composition of claim 1, wherein the first propylene thermoplastic elastomer exhibits a melt index of no greater than 20 grams per 10 minutes.

15. The pressure-sensitive adhesive composition of claim 1, wherein the first propylene thermoplastic elastomer exhibits a melt index of no greater than 10 grams per 1.0 minutes.

16. The pressure-sensitive adhesive composition of claim 1, wherein the first propylene thermoplastic elastomer exhibits a density of no greater than 0.88 grams per cubic centimeter.

17. The pressure-sensitive adhesive composition of claim 1, wherein the first propylene thermoplastic elastomer comprises a polypropylene-polyethylene copolymer.

18. The pressure-sensitive adhesive composition of claim 1 further comprising a second propylene thermoplastic elastomer different from the first propylene thermoplastic elastomer.

19. The pressure-sensitive adhesive composition of claim 18, wherein the second propylene thermoplastic elastomer comprises a propylene-ethylene copolymer.

20. The pressure-sensitive adhesive composition of claim 1 further comprising a hydrogenated styrene block copolymer.

21. The pressure-sensitive adhesive composition of claim 1 further comprising styrene-ethylene-butene-styrene block copolymer, styrene-ethylene-propylene-styrene block copolymer, styrene-ethylene-ethylene-propylene-styrene block copolymer, or a combination thereof.

22. The pressure-sensitive adhesive composition of claim 21 further comprising no greater than 10% by weight of styrene-ethylene-butene-styrene block copolymer, styrene-ethylene-propylene-styrene block copolymer, styrene-ethylene-ethylene-propylene-styrene block copolymer, or a combination thereof.

23. The pressure-sensitive adhesive composition of claim 1 comprising
from 25% by weight to no greater than about 55% by weight of the first tackifying agent; and
from 10% by weight to no greater than about 20% by weight of the first propylene thermoplastic elastomer.

24. The pressure-sensitive adhesive composition of claim 23 further comprising a second tackifying agent, the second tackifying agent exhibiting a softening point of no greater than 100° C., the composition comprising no greater than 20% by weight of the second tackifying agent.

25. The pressure-sensitive adhesive composition of claim 23 further comprising a second polymer, the second polymer exhibiting a viscosity of no greater than 10,000 centipoise at 190° C. and a softening point greater than 90 the composition comprising no greater than 20% by weight of the second polymer.

26. The pressure-sensitive adhesive composition of claim 1, wherein the composition exhibits a viscosity of no greater than 20,000 centipoise at 149° C.

27. An article comprising:
a substrate; and
the pressure-sensitive adhesive composition of claim 1 disposed on the substrate.

28. The article of claim 27, wherein the substrate comprises a nonwoven web.

29. A disposable absorbent article comprising the article of claim 27, the disposable absorbent article comprising a diaper, a personal hygiene article, sanitary napkin, a panty liner, or a combination thereof.

30. The article of claim 27, wherein the substrate comprises a polymer film, a metal film, a metal foil, or a combination thereof.

31. The article of claim 27, wherein
the article is in the form of a label,
the substrate is a first substrate, and
the pressure-sensitive adhesive composition is disposed between the first substrate and a release-coated surface of a second substrate.

32. The pressure-sensitive adhesive composition of claim 1, wherein the composition exhibits an initial peel force to stainless steel of at least 1 Newton.

33. An absorbent article comprising:
a topsheet;
a backsheet;
an absorbent core disposed between the topsheet and the backsheet;
a garment-facing surface; and
the pressure-sensitive adhesive composition of claim 1 disposed on the garment-facing surface of the absorbent article.

34. The pressure-sensitive adhesive composition of claim 1, wherein the first tackifying agent exhibits a softening point of at least 140° C.

35. The pressure-sensitive adhesive composition of claim 1, wherein the first tackifying agent comprises a hydrogenated hydrocarbon resin.

36. The pressure-sensitive adhesive composition of claim 1, wherein the propylene thermoplastic elastomer is selected from the group consisting of polypropylene homopolymer, propylene alpha-olefin copolymer derived from propylene and at least one alpha olefin co-monomer, and combinations thereof.

37. The pressure-sensitive adhesive composition of claim 36, wherein the propylene thermoplastic elastomer is selected from the group consisting of polypropylene, propylene/ethylene copolymer, propylene/ethylene/butene terpolymer, propylene/butene copolymer, propylene/hexane copolymer, propylene/octene copolymer, propylene/norbornene copolymer, and combinations thereof.

38. The pressure-sensitive adhesive composition of claim 1, wherein the propylene thermoplastic elastomer comprises a single-site, metallocene-catalyzed propylene thermoplastic elastomer.

\* \* \* \* \*